United States Patent

Galliani et al.

[11] Patent Number: 5,231,107
[45] Date of Patent: Jul. 27, 1993

[54] DERIVATIVES OF THE OXIME OF 1,2,5,6-TETRAHYDROPYRIDINE 3-CARBOXALDEHYDE, THE PROCESS FOR THEIR PREPARATION, THEIR USE AS MEDICAMENTS AND THE COMPOSITIONS CONTAINING THEM

[75] Inventors: Guilio Galliani; Fernando Barzaghi, both of Monza; Carla Bonetti, Fontanella; Emilio Toja, Milan, all of Italy

[73] Assignee: Roussel Uclaf, Paris, France

[21] Appl. No.: 863,466

[22] Filed: Apr. 1, 1992

Related U.S. Application Data

[60] Continuation of Ser. No. 560,849, Jul. 31, 1990, abandoned, which is a continuation-in-part of Ser. No. 501,889, Mar. 30, 1990, abandoned, which is a division of Ser. No. 234,632, Aug. 22, 1988, Pat. No. 4,921,868.

[30] Foreign Application Priority Data

Aug. 21, 1987 [IT] Italy .................. 21687 A/87

[51] Int. Cl.$^5$ .................. C07D 211/70; A61K 31/44
[52] U.S. Cl. .................. 514/554; 546/326
[58] Field of Search .................. 546/326; 514/354

[56] References Cited

U.S. PATENT DOCUMENTS

| | | | |
|---|---|---|---|
| 3,004,979 | 10/1961 | Druey et al. | 546/338 |
| 4,408,054 | 10/1983 | Strupczewski et al. | 546/226 |
| 4,533,675 | 8/1985 | Brossi et al. | 514/480 |
| 4,710,508 | 12/1987 | Bergmeier et al. | 514/357 |
| 4,786,648 | 11/1988 | Bergmeier et al. | 546/333 |
| 4,902,699 | 2/1990 | Toja et al. | 514/357 |
| 4,921,868 | 5/1990 | Galliani et al. | 514/354 |
| 5,015,655 | 5/1991 | Galliani et al. | 514/413 |
| 5,053,416 | 10/1991 | Toja et al. | 514/340 |

FOREIGN PATENT DOCUMENTS

725633  9/1987  Canada.

OTHER PUBLICATIONS

"Alzheimers Research Moves to Mice" by Jean Marx in Science vol. 253, 266–267 (1991).
Chemical Abstracts, vol. 92, No. 13, Mar. 31, 1980, p. 641, Abstract 110798g.
Jaffe'—Journal of the American Chemical Soc. vol. 76. No. 13 Jul. 5, 1954, pp. 3524–3531.
Chemical Abstracts, vol. 85 (1976) 5172x.
Wagner and Zook Synthetic Organic Chemistry John Wiley & Sons pp. 646–647.
Chemical Abstracts vol. 81 1974 25923p.
March "Advanced Organic Chemistry" 3rd Ed. (1985) pp. 691–700 and 805–806.
Raymond T. Bartus et al., Science, vol. 217, No. 30, Jul. 30, 1982 pp. 408–417 "The Cholinergic Hypothesis of Geriatric Memory . . . ".
Galliani et al., European Journal of Pharmacology, vol. 183 (1990) pp. 1940–1941 "Pharmacological Profile of Ru 35963, A new Muslarinic".
Toja et al., European Journal Medical Chemistry, 1991, 26, pp. 415–422 "Amnesia-Reversal Activity of a Series of 5. Alicoxy-1. Arul . . . ".

Primary Examiner—Thurman K. Page
Assistant Examiner—Jyothsna Denkaz
Attorney, Agent, or Firm—Stevens, Davis, Miller & Mosher

[57] ABSTRACT

Compounds useful in the treatment of patients suffering from senile dementia, Alzheimer's disease or memory defects, of the formula

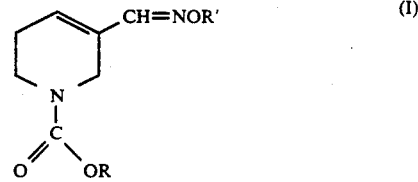

in which R' represents hydrogen, a linear, branched or cyclic alkyl, alkenyl or alkynyl, containing up to 8 carbon atoms, and R represents a linear, branched or cyclic alkyl, alkenyl, or alkynyl, containing up to 18 carbon atoms, possibly substituted, aryl containing up to 14 carbon atoms, possibly substituted, aralkyl containing up to 18 carbon atoms, possibly substituted, as well as their addition salts with organic or mineral acids, and to compounds of formula (I) in which R represents phenyl substituted in the 4 position by Br, F, $CH_3$, $NO_2$ or $C(CH_3)_2C(CH_3)_3$ and R' represents $CH_3$.

7 Claims, No Drawings

DERIVATIVES OF THE OXIME OF 1,2,5,6-TETRAHYDROPYRIDINE 3-CARBOXALDEHYDE, THE PROCESS FOR THEIR PREPARATION, THEIR USE AS MEDICAMENTS AND THE COMPOSITIONS CONTAINING THEM

This application is a continuation of application Ser. No. 07/560,849, filed Jul. 31, 1990, now abandoned which in turn is a continuation-in-part of application Ser. No. 07/501,889 filed Mar. 30, 1990, now abandoned which in turn is a division of application Ser. No. 07/234,632 filed Aug. 22, 1988 (now U.S. Pat. No. 4,921,868 issued May 1, 1990).

The present invention relates to new derivatives of the oxime of 1,2,5,6-tetrahydropyridin-3-carboxaldehyde, their use as medicaments and compositions containing them.

The subject of the invention is the compounds of the formula (I)

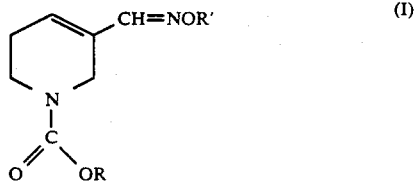

in which R' represents hydrogen, a linear, branched or cyclic alkyl, alkenyl or alkynyl, containing up to 8 carbon atoms, and R represents a linear, branched or cyclic alkyl, alkenyl or alkynyl, containing up to 18 carbon atoms, possibly substituted, aralkyl containing up to 18 carbon atoms, possibly substituted, as well as their addition salts with organic or mineral acids. The invention also relates to specific compounds of formula (I) wherein R represents phenyl substituted in the 4 position by Br, F, $CH_3$, $NO_2$, or $C(CH_3)_2C(CH_3)_3$ and R' represents $CH_3$.

Among the addition salts with acids, there can be cited those formed with mineral acids, such as hydrochloric, hydrobromic, sulphuric or phosphoric acids, or with organic acids such as formic, acetic, propionic, benzoic, maleic, fumaric, succinic, tartaric, citric, oxalic, glyoxylic, aspartic, alkanesulphonic such as methane- or ethane-sulphonic, arylsulphonic such as benzene- or paratoluene-sulphonic acids.

When R represents linear or branched alkyl, it is preferred to be methyl, ethyl, n-propyl, isopropyl, n-butyl, isobutyl, n-pentyl, n-hexyl, tert-butyl, neopentyl or adamantyl.

When R' represents linear or branched alkyl, it is preferred to be methyl, ethyl, n-propyl, isopropyl, n-butyl, isobutyl, n-pentyl, tert-butyl, tert-pentyl, neopentyl or n-hexyl.

When R or R' represents alkenyl or alkynyl, it is preferred to be an ethylene radical such, for example, as vinyl, allyl, 1,1-dimethylallyl or but-2-enyl, or an acetylene radical such, for example, as ethynyl or propynyl.

When R or R' represents a cyclic alkyl radical, it is preferred to be cyclopropyl, cyclobutyl, cyclopentyl, cyclohexyl, cyclopropylmethyl, cyclobutylmethyl, cyclopentylmethyl or cyclohexylmethyl.

When R is a substituted alkyl, the substituent is preferred to be an alkylsulphonyl containing up to 18 carbon atoms or the radical Si-$Alk_3$ in which Alk represents an alkyl containing up to 4 carbon atoms.

When R represents aryl, it is preferred to be phenyl.

When R represents aralkyl, it is preferred to be phenalkyl, e.g., benzyl or phenethyl.

The aryl or aralkyl can include one or more substituents chosen from halogen such as chlorine or bromine, linear or branched alkyl such as methyl, ethyl, linear or branched propyl, linear or branched butyl, alkoxy such as methoxy, ethoxy, linear or branched propoxy, and linear or branched butoxy.

When R represents an alkyl substituted with an alkylsulphonyl, it is preferred to be $CH_2SO_2CH_3$, —$CH_2CH_2SO_2CH_3$ or $CH_2CH_2CH_2SO_2CH_3$.

Among the preferred compounds of the invention, there can be cited the compounds in which R' represents linear alkyl, alkenyl or alkynyl containing up to 4 carbon atoms, such, for example, as methyl.

There can also be cited the compounds in which R represents linear alkyl, alkenyl or alkynyl, containing up to 4 carbon atoms, such, for example, as methyl, or also allyl or phenyl, a substituted phenyl such, for example, as 4-chlorophenyl, isopropylphenyl or 3,4-dimethoxyphenyl, as well as their addition salts with mineral or organic acids.

As more preferred compounds of the invention, there can be cited the compounds described in examples 2, 4, 6, 12, 13 and 14 and more particularly the methyl ether of (4-chlorophenyl-oxy-carbonyl-1,2,5,6-tetrahydropyridin-3-carboxaldehyde oxime, as well as their addition salts with organic or mineral acids.

The products of the invention present very interesting pharmacological properties and notably an important cholinomimetic activity by oral route which has a long duration of action.

In addition, the products present a strong dissociation between the central activity and the peripheral activity.

It is well known that difficulties of learning and of memory in elderly people are connected above all with a defect of the central cholinergic system, in particular in senile dementia and Alzheimer's disease.

It is therefore evident that products having a central cholinergic action can be employed in the therapeutic treatment of these maladies (Bartus, R.I. Science 217, 408, 1982).

It has been shown that arecoline injected by intravenous route has a positive effect on patients having a memory defect (Sitaram N. et al, Science 201, 274, 1978) (Christie J. E., et al Brit. J. Psychiatry, 138, 46, 1981).

A limitation to the therapeutic use of arecoline is connected with the fact that this product has very weak activity by oral route and a short duration of action.

The products which are the subject of the invention have shown, after administration by oral route, a central cholinomimetic activity very much greater than that of arecoline and with a longer duration of action.

Therefore, the invention has as its subject the products as medicaments useful in particular in the treatment of Alzheimer's disease or senile dementia and also in the treatment of memory disorders.

More particularly, the subject of the invention, as medicaments, is the compounds of examples 2, 4, 6, 12, 13 and 14, as well as their addition salts with pharmaceutically acceptable acids.

The usual posology is variable according to the affection concerned, the subject treated and the administration routes; it can be between 10 mg and 300 mg/day, preferably between 50 mg and 200 mg/day, for example, between 15 and 150 mg/day, preferably between 50 mg and 100 mg/day in one or more doses for the product of example 12 administered by oral route.

The present invention also has as its subject the pharmaceutical compositions containing at least one product with the formula (I) as active principle.

The pharmaceutical compositions according to the invention can be solid or liquid, and are present in the pharmaceutical forms currently used in human medicine, such, for example, as plain or sugar-coated tablets, capsules, granules, suppositories and injectable preparations; they are prepared according to the usual methods.

The active principle or principles can be incorporated in them with the excipients usually employed in those pharmaceutical compositions, such as talc, gum arabic, lactose, starch, magnesium stearate, cocoa, aqueous or non-aqueous vehicles, fatty substances of animal or vegetable origin, paraffin derivatives, glycols, the various wetting, dispersing or emulsifying agents and preservatives.

The invention also has as its subject a process for the preparation of the compounds with the formula (I) characterized in that a compound with the formula (II):

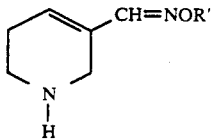

in which R' retains the same significance as previously, is submitted to the action of an alkoxycarbonylation agent able to introduce the radical —$CO_2R$, R being defined as previously, so as to obtain the corresponding compound with the formula (I), which, if desired, is submitted to the action of an acid in order to form its salt.

In a preferred way of carrying out the invention process, the alkoxycarbonylation agent is a product with the formula (III):

in which X represents a halogen atom, a paranitrophenoxy radical or the radical

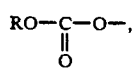

R being defined as previously.

The invention also has as its subject a process characterized in that a compound with the formula (IV):

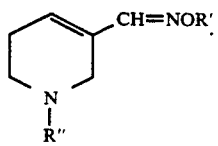

in which R" represents a linear, branched or cyclic radical, saturated or unsaturated, containing up to 4 carbon atoms or an aralkyl containing up to 14 carbon atoms, is submitted to the action of an agent able to cleave the group R" and to introduce the group

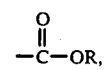

R being defined as previously, in order to obtain the corresponding compound with the formula (I):

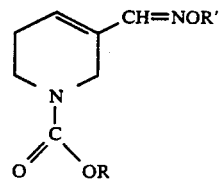

which, if desired, is submitted to the action of an acid to form its salt.

In a preferred way of realizing [the invention products] a compound is used with the formula (III):

operating hot.

The starting products with the formulae (II) and (IV) are described and claimed in the European patent EP 0239445.

The following examples illustrate the invention, nevertheless without limiting it.

EXAMPLE 1

Methyl ether of 1-methoxycarbonyl-1,2,5,6-tetrahydropyridin-3-carboxaldehyde oxime.

To a solution of 1.5 g of 1,2,5,6-tetrahydropyridin-3-carboxaldehyde-O-methyl oxime prepared as indicated in the patent application EP 239445, in 40 cm$^3$ of benzene, 1.5 cm$^3$ of triethylamine is added at 10° C., and, slowly, 0.83 cm$^3$ of methyl chloroformate. After agitating for 30 minutes at ambient temperature, washing with 15 cm$^3$ of 5% hydrochloric acid and then with water, evaporating to dryness under reduced pressure, then distilling the residue at 140° C. under 0.05 mbar, 1.91 g of the expected product is obtained. m.p. 37° C.

Analysis: $C_9H_{14}N_2O_3$: Calculated: C% 54.53; H% 7.12; N% 14.13. Found: C% 54.31; H% 7.17; N% 14.00.

EXAMPLE 2

Methyl ether of 1-ethoxycarbonyl-1,2,5,6-tetrahydropyridin-3-carboxaldehyde oxime.

Method A

To a solution of 3.6 g of 1-benzyl-1,2,5,6-tetrahydropyridin-3-carboxaldehyde-O-methyloxime prepared as indicated in the patent application EP 239445, in 30 cm$^3$ of dichloroethane, 2 cm$^3$ of ethyl chloroformate is added, and the whole is kept at reflux for 3 hours. The reactive mixture is cooled and the organic phase is washed with 20 cm$^3$ of hydrochloric acid at 5%, then twice with 25 cm$^3$ of water. The solvent is evaporated, the residual oil is distilled at 150° C. under 0.05 mbar, and 1.5 g of the expected product is obtained.

Analysis: $C_{10}H_{16}N_2O_3$: Calculated: C% 56.59; H% 7.60; N% 13.20. Found: C% 56.82; H% 7.66; N% 13.04.

Method B

To a solution of 3.75 g of 1,2,5,6-tetrahydropyridin-3-carboxaldehyde-O-methyloxime prepared as indicated in the patent application EP 239445, in 60 cm$^3$ of benzene, 3.75 cm$^3$ of triethylamine and 2.7 cm$^3$ of ethyl chloroformate are added at a temperature not exceeding 10° C. The mixture is agitated for 1 hour at embient temperature, then 20 cm$^3$ of water is added, followed by decanting, extracting with benzene, and evaporating to dryness under reduced pressure. The residue is chromatographed on silica (eluent: ethyl acetate–toluene, 1-1). The residue is distilled at 160°–165° C. under 0.07 mbar. 5.32 g of the expected product is obtained.

Analysis: $C_{10}H_{16}N_2O_3$: Calculated: C% 56.59; H% 7.60; N% 13.20. Found: C% 56.41; H% 7.54; N% 13.31.

EXAMPLE 3

Methyl ether of 1-n-propyloxycarbonyl-1,2,5,6-tetrahydropyridin-3-carboxaldehyde oxime To a solution of 1.5 g of 1,2,5,6-tetrahydropyridin-3-carboxaldehyde-O-methyloxime dissolved in 60 cm$^3$ of benzene, 1.5 cm$^3$ of triethylamine is added and while maintaining the temperature between 5° and 10° C., 1.23 cm$^3$ of propyl chloroformate is added slowly. After 30 minutes at ambient temperature, and washing with 20 cm$^3$ of 1N hydrochloric acid and then with water, the solvent is evaporated off under reduced pressure, and the residue is distilled at 170° C. under 0.07 mbar. 2.3 g of the expected product is obtained.

Analysis: $C_{11}H_8N_2O_3$: Calculated: C% 58.39; H% 8.02; N% 12.38. Found: C% 58.12; H% 8.06; N% 12.12.

EXAMPLE 4

Methyl ether of 1-allyloxycarbonyl-1,2,5,6-tetrahydropyridin-3-carboxaldehyde oxime To a solution of 1,2,5,6-tetrahydropyridin-3-carboxaldehyde-O-methyloxime in 40 cm$^3$ of benzene, 1.5 cm$^3$ of triethylamine and 1.17 cm$^3$ of 2-propenyl chloroformate are added. The mixture is agitated for 30 minutes at ambient temperature, then treated with 20 cm$^3$ of 5% hydrochloric acid, then twice with 20 cm$^3$ of water. The solvent is evaporated off, then the residue is distilled at 200° C. under 0.08 mbar. 2.25 g of the expected product is obtained.

Analysis: $C_{11}H_{16}N_2O_3$: Calculated: C% 58.91; H% 7.19; N% 12.49. Found: C% 58.96; H% 7.25; N% 12.41.

EXAMPLE 5

Methyl ether of 1-benzyloxycarbonyl-1,2,5,6-tetrahydropyridin-3-carboxaldehyde oxime

Method A

To a solution of 8 g of 1-benzyl-1,2,5,6-tetrahydropyridin-3-carboxaldehyde-O-methyl oxime in 100 cm$^3$ of benzene, there is added 23 cm$^3$ of benzyl chloroformate at 50% in toluene, and the whole is taken to boiling point for 4 hours, then cooled, washed with 2N hydrochloric acid and then with water. The solvent is evaporated off under reduced pressure, then the residue is distilled at 200° C. under. 0.05 mbar. 4.1 g of the expected product is obtained.

Method B

To a solution of 1.5 g of 1,2,5,6-tetrahydropyridin-3-carboxaldehyde-O-methyl oxime in 20 cm$^3$ of benzene, and 1,08 g of triethylamine, there is added 3,4 cm$^3$ of benzylchloroformate at 50% in toluene, and the whole is agitated for one hour at ambient temperature, washed with 2N hydrochloric acid and with water. The solvent is evaporated off under reduced pressure, then the residue is distilled at 230° C. under 0.06 mbar. 2.1 g of the expected product is obtained.

Analysis: $C_{14}H_{16}N_2O_3$: Calculated: C% 65.54; H% 6.72; N% 10.14. Found: C% 65.68; H% 6.61; N% 10.21.

EXAMPLE 6

Methyl ether of 1-phenyloxycarbonyl-1,2,5,6-tetrahydropyridin-3-carboxaldehyde oxime

Method A

To a solution of 3.3 g of 1-methyl-1,2,5,6-tetrahydropyridin-3-carboxaldehyde-O-methyloxime, prepared as indicated in the patent application EP 239445, in 30 cm$^3$ of dichlorethane, 4.5 g of phenyl chloroformate is added, and the whole is heated for 3 hours to reflux. The insoluble matter (hydrochloride of the starting product) is filtered off, then the remainder is evaporated to dryness under reduced pressure. The residue is chromatographed on silica (eluent: benzene–ethyl acetate 8-2). 4 g of the expected product is obtained after distilling at 220° C. under 0.06 mbar.

Method B

To a solution of 3 g of 1-ethyl-1,2,5,6-tetrahydropyridin-3-carboxaldehyde-O-methyloxime, prepared as indicated in the patent application EP 239445, in 30 cm$^3$ of dichlorethane, 4.7 cm$^3$ of phenyl chloroformate is added. The whole is taken to reflux for 3 hours, treated with 20 cm$^3$ of 5% hydrochloric acid, then twice with 20 cm$^3$ of water. The solvent is evaporated off, then the remainder is taken up with diethyl ether, the insoluble matter is filtered off, and the filtrate is evaporated to dryness. The residual oil is distilled at 210° C. under 0.03 mbar, so obtaining 2.18 g of the expected product Analysis: $C_{14}H_{16}N_2O_3$: Calculated: C% 64.6; H% 6.20; N% 10.76. Found: C% 64.72; H% 6.35; N% 10.65.

EXAMPLE 7

Methyl ether of [1-(2-methylsulphonyl)ethoxy-carbonyl]-1,2,5,6-tetrahydropyridin-3-carboxaldehyde oxime To a solution of 1.5 g of 1,2,5,6-tetrahydropyridin-3-carboxaldehyde-O-methyloxime in 40 cm$^3$ of anhydrous benzene and 1.5 cm$^3$ of triethylamine cooled to 5° C., 3.1 g of (2-methylsulphonyl)ethyl-4-nitrophenyl carbonate is added. The reaction is continued for 1 hour at ambient temperature, then the organic phase is washed with water and evaporated to dryness under reduced pressure. The residue is chromatographed on silica (eluent: ethyl acetate), and 1.6 g of the expected product is obtained, crystallized from benzene. m.p. 93°–94° C.

Analysis: $C_{11}H_{18}N_2O_5S$: Calculated: C% 45.50; H% 6.25; N% 9.65. Found: C% 45.63; H% 6.29; N% 9.61.

EXAMPLE 8

Methyl ether of 1-adamantyloxycarbonyl-1,2,5,6-tetrahydropyridin-3-carboxaldehyde oxime To a solution of 1.5 g of 1,2,5,6-tetrahydropyridin-3-carboxaldehyde-O-methyloxime in 40 cm$^3$ of benzene and 1.5 cm$^3$ of triethylamine, 2.13 g of adamantyl fluoroformate is added at 5° C. After 15 minutes at ambient temperature, washing with 2N hydrochloric acid and then with water, evaporating to dryness under reduced pressure and crystallizing from hexane, 2.6 g of the expected product is obtained. m.p. 105°–106° C.

Analysis: $C_{18}H_{26}N_2O_3$: Calculated: C% 67.90; H% 8.23; N% 8.80. Found: C% 68.02; H% 8.28; N% 8.76.

EXAMPLE 9

Methyl ether of 1-isopropyloxycarbonyl-1,2,5,6-tetrahydropyridin-3-carboxaldehyde oxime To a mixture of 1.4 g of 1,2,5,6-tetrahydropyridin-3-carboxaldehyde-O-methyloxime and 1.01 g of anhydrous triethylamine in 30 cm$^3$ of benzene, 1.22 g of isopropyl chloroformate in solution in benzene is added at 10° C. After agitating for 30 minutes at ambient temperature, decanting, washing the organic phase, evaporating to dryness and chromatographing the residue on silica (eluent: toluene–ethyl acetate, 8–2), a residue is obtained which is distilled at 180° C. under 0.08 mbar. 1.35 g of the expected product is obtained, m.p. 40°–41° C.

Analysis: $C_{11}H_{18}N_2O_3$: Calculated: C% 58.39; H% 8.02; N% 12.38. Found: C% 58.19; H% 8.13; N% 12.54.

EXAMPLE 10

Methyl ether of 1-butyloxycarbonyl 1,2,5,6-tetrahydropyridin-3-carboxaldehyde oxime To a solution of 1.5 g of 1,2,5,6-tetrahydropyridin-3-carboxaldehyde-O-methyloxime in 20 cm$^3$ of benzene and 1.2 g of triethylamine, 1.46 g of butyl chloroformate is added at 10° C. After agitating for 2 hours at ambient temperature, washing with 2N hydrochloric acid, then evaporating to dryness and distilling the residue at 220° C. under 0.08 mbar, 1.85 g of the expected product is obtained.

Analysis: $C_{12}H_{20}N_2O_3$: Calculated: C% 59.98; H% 8.39; N% 11.66. Found: C% 59.72; H% 8.49; N% 11.77.

EXAMPLE 11

Methyl ether of 1-[2-(phenyl)-ethyloxy]-carbonyl-1,2,5,6-tetrahydropyridin-3-carboxaldehyde oxime To a mixture of 1.4 g of 1,2,5,6-tetrahydropyridin-3-carboxaldehyde-O-methyloxime and 1.01 g of triethylamine in 40 cm$^3$ of benzene, 1.85 g of [(2-phenyl)ethyl] chloroformate is added at +10° C. After 30 minutes at ambient temperature, washing with dilute hydrochloric acid, then evaporating to dryness, the residue is purified by chromatography on alumina (eluent: cyclohexane–ethyl acetate 9–1), then distilled under 0.07 mbar at 250° C. 2.2 g of the expected product is obtained.

Analysis: $C_{16}H_{20}N_2O_3$: Calculated: C% 66.65; H% 6.99; N% 9.72. Found: C% 66.51; H% 7.10; N% 9.79.

EXAMPLE 12

Methyl ether of 1-parachlorophenyloxy-carbonyl-1,2,5,6-tetrahydropyridin-3-carboxaldehyde oxime To a mixture of 1.4 g of 1,2,5,6-tetrahydropyridin-3-carboxaldehyde-O-methyloxime and 1.01 g of triethylamine in 40 cm$^3$ of benzene, 1.91 g of p-chlorophenyl chloroformate. (J. Am. Chem. Soc. 47, 2607) is added at +10° C. in 30 cm$^3$ of benzene. After 3 hours at ambient temperature, washing with dilute hydrochloric acid, then evaporating to dryness, the residue is purified by chromatography on alumina (eluent: cyclohexane–ethyl acetate 7–3). 1.9 g of the expected product is obtained, crystallized from cyclohexane, m.p. 96°–98° C.

Analysis: $C_{14}H_{15}N_2O_3$: Calculated: C% 57.05; H% 5.13; N% 9.51. Found: C% 56.78; H% 4.97; N% 9.37.

EXAMPLE 13

Methyl ether of 1-p-isopropylphenyloxycarbonyl-1,2,5,6-tetrahydropyridin-3-carboxaldehyde oxime To 1.4 g of 1,2,5,6-tetrahydropyridin-3-carboxaldehyde-O-methyloxime in 40 cm$^3$ of benzene and 1.01 g of triethylamine, 1.99 g of p-isopropylphenyl chloroformate (Brit. Pat. 798 659 (1978)) is added at 10° C. in solution in 20 cm$^3$ of benzene. After 1 night at ambient temperature, washing with dilute hydrochloric acid, then evaporating to dryness, the residue is purified by chromatography on alumina (eluent: cyclohexane–ethyl acetate 9–1). After crystallizing from cyclohexane, 2 g of the expected product is obtained. m.p. 100°–102° C.

Analysis: $C_{17}H_{22}N_2O_3$: Calculated: C% 67.53; H% 7.33; N% 9.27. Found: C% 67.70; H% 7.44; N% 9.14.

EXAMPLE 14

Methyl ether of 1-(3,4-dimethoxyphenyloxy-carbonyl-1,2,5,6-tetrahydropyridin-3-carboxaldehyde oxime To a solution of 1.2 g of 1,2,5,6-tetrahydropyridin-3-carboxaldehyde-O-methyloxime in 20 cm$^3$ of benzene and 1.2 cm$^3$ of triethylamine, 1.86 g of 3,4-dimethoxyphenyl chloroformate is added, with agitation for 45 minutes, then washing with 10% hydrochloric acid and evaporating to dryness. The residue is chromatographed on alumina (eluent: cyclohexane–ethyl acetate 7–3). 1.85 g of the expected product is obtained, crystallized from cyclohexane. m.p. 143°–145° C.

Analysis: $C_{16}H_{20}N_2O_5$: Calculated: C% 59.99; H% 6.29; N% 8.75. Found: C% 60.24; H% 6.21; N% 8.61.

EXAMPLE 15

2-propynyl ether of 1-ethyloxycarbonyl-1,2,5,6-tetrahydropyridin-3-carboxaldehyde oxime.

To a solution of 1,2,5,6-tetrahydropyridin-3-carboxaldehyde-O-(2-propynyl) oxime, prepared as indicated in patent application EP 239,445, in 50 cm$^3$ of of benzene, 1.42 cm$^3$ of triethylamine and 1.02 cm$^3$ of 95% ethylchloroformate are added at 5° C., with agitation for 30 minutes, then washing with water and evaporating to dryness under reduced pressure. The residue is purified by chromatography on alumina (eluent: benzene–diethyl ether, 1–1), then evaporated to dryness, taken up with benzene, treated with sodium sulphate and active carbon, filtered, and taken to dryness under reduced pressure. 1.95 g of the expected product is obtained, m.p. 55° C.

Analysis: $C_{12}H_{16}N_2O_3$: Calculated: C% 61.00; H% 6.83; N% 11.86. Found: C% 61.23; H% 6.66; N% 11.71.

EXAMPLE 16

Methyl ether of 1-tertbutyloxycarbonyl-1,2,5,6-tetrahydropyridin-3-carboxaldehyde oxime To a solution of 1.5 g of 1,2,5,6-tetrahydropyridin-3-carboxaldehyde-O-methyloxime in 40 cm$^3$ of benzene, 1.5 cm$^3$ of triethylamine is added, the mixture is cooled to 5° C. and 2.33 g of tertbutyl carbonate is added. After 10 minutes at ambient temperature, washing with 2N hydrochloric acid and then with water, evaporating under reduced pressure, then isolating the product by distilling at 150° C. under 0.07 mbar, 2.2 g of the expected product is obtained.

Analysis: $C_{12}H_{20}N_2O_3$: Calculated: C% 59.83; H% 8.5; N% 11.49. Found: C% 60.00; H% 8.39; N% 11.66.

EXAMPLE 17

Methyl ether of 1-(2-trimethylsilylethyloxy)carbonyl-1,2,5,6-tetrahydropyridin-3-carboxaldehyde oxime To a solution of 1.5 g of 1,2,5,6-tetrahydropyridin-3-carboxaldehyde-O-methyloxime in 40 cm$^3$ of benzene and 1.5 cm$^3$ of triethylamine, 3.03 g of paranitrophenyl carbonate of (2-trimethylsilyl)ethyl is added, at 5° C., with agitation for 3 hours at ambient temperature, then washing with water and evaporating under vacuum. After purifying by chromatographing on silica (eluent: benzene-diethyl ether 1-1), the expected product is isolated by distilling at 220° C. under 0.08 mbar. 2.3 g of the expected product is obtained.

Analysis: $C_{13}H_{24}N_2O_3Si$: Calculated: C% 54.89; H% 8.50; N% 9.85. Found: C% 54.85; H% 8.59; N% 9.76.

EXAMPLE 18

Synthesis of 1-(4-nitrophenyloxycarbonyl)-1,2,5,6-tetrahydropyridine-3-carboxaldehyde-O-methyloxime.

A solution of 97% 4-nitrophenyl chloroformate (1.5 g, 7.22 mmoles) in dichloromethane (15 mL) was added at 0° C. to a stirred solution of 1,2,5,6-tetrahydropyridine-3-carboxaldehyde-O-methyloxime (0.92 g, 6.6 mmoles) and triethylamine (0.92 mL, 6.6 mmoles) in dichloromethane (20 mL). The reaction mixture was then stirred at room temperature for 20 minutes, the solvent was evaporated and the residue was partitioned between water and ethyl acetate. The organic layer was dried (Na$_2$SO$_4$) and evaporated. The solid was recrystallized from benzene-cyclohexane to give 1.9 g (95%) of the desired product with mp 109°-110° C.

| | | C | H | N |
|---|---|---|---|---|
| Analysis ($C_{14}H_{15}N_3O_5$) | Calcd | 55.08 | 4.95 | 13.76 |
| | Found | 54.97 | 5.12 | 13.67 |

EXAMPLE 19

Synthesis of 1-(4-bromophenyloxycarbonyl)-1,2,5,6-tetrahydropyridine-3-carboxaldehyde-O-methyloxime.

A solution of 4-bromophenylchloroformate (2.12 g, 8.6 mmoles) in dichloromethane (15 mL) was added under nitrogen at 0° C. to a stirred solution of 1,2,5,6-tetrahydropyridine-3-carboxaldehyde-O-methyloxime (1.1 g, 7.8 mmoles) and triethylamine (1.1 mL, 7.8 mmoles) in dichloromethane (15 mL). The reaction mixture was stirred at room temperature for 20 minutes, washed with water and the organic layer was dried (Na$_2$SO$_4$) and evaporated. The residue was triturated with cyclohexane to afford 2.46 g (92%) of a white solid with mp 93°-94° C.

| | | C | H | N |
|---|---|---|---|---|
| Analysis ($C_{14}H_{15}BrN_2O_3$) | Calcd | 49.58 | 4.46 | 8.26 |
| | Found | 49.73 | 4.50 | 8.15 |

EXAMPLE 20

Synthesis of 1(4-fluorophenyloxycarbonyl)-1,2,5,6-tetrahydropyridine-3-carboxaldehyde-O-methyloxime.

A solution of 4-fluorophenylchloroformate (1.4 mL, 10.3 mmoles) in dichloromethane (15 mL) was added under nitrogen at 0° C. to a stirred solution of 1,2,5,6-tetrahydropyridine-3-carboxaldehyde-O-methyloxime (1.3 g, 9.3 mmoles) and triethylamine (1.3 mL, 9.3 mmoles) in dichloromethane (20 mL). The reaction mixture was stirred at room temperature for 20 minutes, washed with water and the organic layer was dried (Na$_2$SO$_4$) and evaporated. The residue was triturated with cyclohexane to afford 2.5 g (96%) of a white solid with mp 100°-101° C.

| | | C | H | N |
|---|---|---|---|---|
| Analysis ($C_{14}H_5FN_2O_3$) | Calcd | 60.43 | 5.43 | 10.07 |
| | Found | 60.35 | 5.45 | 10.02 |

EXAMPLE 21

Synthesis of 1-(4-methylphenyloxycarbonyl)-1,2,5,6-tetrahydropyridine-3-carboxaldehyde-O-methyloxime.

A solution of p-tolylchloroformate (1.5 mL, 10.3 mmoles) in dichloromethane (15 mL) was added under nitrogen at 0° C. to a stirred solution of 1,2,5,6-tetrahydropyridine-3-carboxaldehyde-O-methyloxime (1.3 g, 9.3 mmoles) and triethylamine (1.3 mL, 2.3 mmoles) in dichloromethane (20 mL). The reaction mixture was stirred at room temperature for 20 minutes, the solvent was evaporated and the residue was partitioned between water and ethylacetate. The organic layer was dried (Na$_2$SO$_4$) and evaporated. The solid was triturated with cyclohexane to afford 2.3 g (91%) of a white solid with mp 70°-71° C.

| | | C | H | N |
|---|---|---|---|---|
| Analysis ($C_{15}H_{18}N_2O_3$) | Calcd | 65.68 | 6.61 | 10.21 |
| | Found | 65.73 | 6.66 | 10.20 |

EXAMPLE 22

Synthesis of 1-[4-(1,1,3,3-tetramethylbutyl) phenyloxycarbonyl]-1,2,5,6-tetrahydropyridine-3-carboxaldehyde-O-methyloxime.

A solution of 4-(1,1,3,3-tetramethylbutyl)phenylchloroformate (1.77 g, 6.5 mmoles) in dichloromethane (10 mL) was added under nitrogen at 0° C. to a stirred solution of 1,2,5,6-tetrahydropyridine-3-carboxaldehyde-O-methyloxime (0.94 g, 6.7 mmoles) and triethylamine (0.94 mL, 6.7 mmoles) in dichloromethane (10 mL). The reaction mixture was stirred at room temperature for 20 minutes, the solvent was evaporated and the residue was partitioned between ethyl acetate and 1% aqueous HCl to remove unreacted starting material. The organic layer was dried ($Na_2SO_4$) and evaporated. The residue was recrystallized from EtOH. $H_2O$ to afford 2.3 g (94%) of a white solid with mp 91°-93° C.

| | | C | H | N |
|---|---|---|---|---|
| Analysis ($C_{22}H_{32}N_2O_3$) | Calcd | 70.94 | 8.66 | 7.52 |
| | Found | 71.62 | 8.79 | 7.38 |

Example of Pharmaceutical Compositions a) Tablets have been prepared answering to the following formula:

| | |
|---|---|
| Product of example 12 | 50 mg |
| Excipient q.s. for a tablet finished at | 300 mg |
| (detail of excipient: lactose, corn starch, treated starch, rice starch, magnesium stearate, talc). | | b) Capsules have been prepared answering to the following formula:

| | |
|---|---|
| Product of example 12 | 60 mg |
| Excipient q.s. for a capsule finished at | 300 mg |
| (detail of excipient: talc, magnesium stearate, aerosil). | |

PHARMACOLOGICAL STUDY

Acute Toxicity

The test was carried out on male mice ($CD_1$ Charles Rivers), of 22 to 24 g, without food for 16 hours. The products are administered by oral route at doses of 1000, 500, 250, 125, and 62 mg/kg. The mortality is noted during the 7 days following the treatment. The results are shown in Table 1.

TABLE 1

| Example | $LD_{50}$ mg/kg |
|---|---|
| 2 | 175 |
| 4 | 175 |
| 6 | 500 |
| 13 | >1000 |
| 12 | >1000 |
| 14 | 175 |
| 18 | 500 |
| 19 | >1000 |
| 20 | 500 |
| 21 | 250 |
| 22 | 500 |
| Arecoline HBr | >600 |

Test of Ileum Isolated from Guinea-pig

Pieces of ileum are removed from guinea-pigs killed by decapitation. The isolated ileum is placed in 10 cm³ of Tyrode solution at 37° C. and aerated with a mixture of oxygen (95%) and carbon dioxide gas (5%). The contractions due to the products are registered by means of a detector connected to a polygraph. The products to be tested are added at concentrations between $1.10^{-3}$M and $1.10^{-8}$M/l.

The products presenting a contracting effect are tested vis-a-vis atropine and hexamethonium in order to establish if the activity is of "muscarine" or "nicotine" type.

The possible antagonist activity of the products is tested vis-a-vis acetylcholine.

The agonist activity is expressed in $pD_2$ (negative logarithm of the dose which produces 50% of the maximum effect).

The antagonist activity is expressed in $DE_{50}$ (dose reducing by 50% the maximum response induced by acetylcholine). The results are shown in Table 2.

TABLE 2

| Example | PD 2 | $DE_{50}$ mg/kg |
|---|---|---|
| 2 | 4.47 | — |
| 4 | <4 | $6.0 \times 10^{-4}$ |
| 6 | <4 | $>1 \times 10^{-4}$ |
| 13 | <4 | $>1 \times 10^{-4}$ |
| 12 | <4 | $>1 \times 10^{-4}$ |
| 14 | <4 | $>1 \times 10^{-4}$ |
| 18 | <4 | |
| 19 | <4 | |
| 20 | <4 | |
| 21 | <4 | |
| 22 | 4 | |
| Arecoline | 6.48 | |

Diarrhoeic Activity

The test is carried out on male mice ($CD_1$ Charles Rivers) weighing 25 to 30 g, which have fasted for 6 hours. The product dissolved at 5% in methocel is administered by oral route by means of an oesophage probe.

Control animals receive only the excipient.

After treatment, the animals are placed separately in cages of which the base is covered with blotting paper, and they are put under observation for 30, 60, 120 and 180 minutes.

The sheets of absorbent paper are changed after each observation.

The consistency of the feces is evaluated according to the method of Randall and Baruth (Arch. Int. Pharmacodyn. 220, 94, 1976) according to the following scale of values.

0: consistency firm,
1: feces slightly soft, with or without a damp halo,
2: feces slightly soft, with a well-defined circle of humidity,
3: feces soft with a large circle of humidity,
4: feces without consistency with a very large circle of humidity.

For each product, the dose is noted which causes diarrhoea in 50% of the animals according to the method of Miller and Tainter (Proc. Soc. Exp. Biol. Med., 57, 261, 1944). The results are shown in Table 3.

TABLE 3

| Example | $DE_{50}$ mg/kg |
|---|---|
| 2 | 25 |
| 4 | 3 |
| 6 | 100 |
| 13 | >50 |
| 12 | >50 |
| 14 | >50 |
| 18 | >50 |
| 19 | >50 |
| 20 | >50 |
| 21 | >50 |
| 22 | >50 |
| arecoline | 35 |

Hypothermic Activity

The test is carried out on male mice ($CD_1$ Charles Rivers) weighing 25-30 g, which have fasted for 6 hours.

The temperature of the body is noted by means of a thermocouple inserted about 1.5 cm in the rectum and connected to an electric temperature recorder.

The products are administered by oral or sub-cutaneous route and the temperatures are noted at the instant 0 and at 30 minutes, 1 hour, 2 hours and 2-and-a-half hours after treatment.

The degree of hypothermia is evaluated as the difference between the treated animals and the controls, and the dose necessary to reduce the body temperature by 1° C. is noted. The results are shown in Table 4.

TABLE 4

| Example | Effective dose (−1° C.) in mg/kg | |
|---|---|---|
| | O.R. | SC.R |
| 2 | 3.9 | 3.6 |
| 4 | 1.6 | 1.8 |
| 6 | 4.6 | 2.3 |
| 13 | 3.4 | 8.8 |
| 12 | 2.2 | 2.9 |
| 14 | 0.7 | 0.7 |
| 18 | 4.0 | 5.0 |
| 19 | 1.7 | 1.3 |
| 20 | 3.2 | 1.5 |
| 21 | 1.5 | 1.2 |
| 22 | 7 | 15 |
| arecoline | 194 | 3.0 |

Variation of the Body Temperature

The duration of action of the products is determined, using the doses able to reduce the temperature by 1° to 1.5° C. See Table 5.

TABLE 5

| | | | Variations of the body temperature (°C.) | | | | |
|---|---|---|---|---|---|---|---|
| | Dose | | Treatment Time in Minutes | | | | |
| Example | mg/kg | Administration | 0 | 30 | 60 | 120 | 180 |
| 2 | 5. | os | +0.2 | −1.2** | −1.1** | −0.1 | ±0. |
| | 5. | sc | +0.2 | −1.5** | −1.4** | −0.1 | ±0. |
| 4 | 2. | os | −0.1 | −1.2** | −1.1** | −0.1 | −0.1 |
| | 2. | sc | −0.1 | −0.9** | −1.0** | −0.2 | −0.1 |
| 6 | 7.5 | os | −0.1 | −1.1** | −1.6** | −0.6** | ±0. |
| | 3.5 | sc | −0.1 | −0.6** | −1.4** | −0.9** | 0.1 |
| 13 | 6.25 | os | +0.2 | −0.4** | −1.6** | −0.4** | −0.1 |
| | 12.5 | sc | +0.2 | ±0. | −0.7** | −1.4** | −1.1** |
| 12 | 3.12 | os | +0.1 | −0.9** | −1.4** | −0.3* | ±0. |
| | 3.12 | sc | −0.1 | −0.1 | −1.1** | −1.2** | −0.5** |
| 14 | 1. | os | +0.1 | −1.1** | −1.4** | −0.2 | +0.1 |
| | 1. | sc | +0.2 | −0.7** | −1.3** | −0.5** | ±0. |
| Arecoline, HBr | 200 | os | +0.1 | −1.1** | −1.0** | −0.2 | −0.1 |
| | 3.5 | sc | −0.1 | −1.5** | −0.1 | +0.2 | +0.2 |

**Values differing from the controls in a significant manner (p <0.05); (*p <0.01)

What is claimed:

1. A compound of the formula (I):

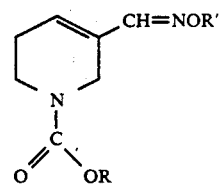

in which R represents phenyl substituted in the 4 position by Br, F, $CH_3$, $NO_2$ or $C(CH_3)_2C(CH_3)_3$ and R' represents $CH_3$, or a pharmaceutically acceptable acid addition salt thereof.

2. The compound of claim 1 wherein R represents phenyl substituted by Br, or an addition salt with an organic or a mineral acid thereof.

3. The compound of claim 1 wherein R represents phenyl substituted by F, or an addition salt with an organic or a mineral acid thereof.

4. The compounds of claim 1 wherein R represents phenyl substituted by $CH_3$, or an addition salt with an organic or a mineral acid thereof.

5. The compound of claim 1 wherein R represents phenyl substituted by $NO_2$, or an addition salt with and organic or a mineral acid thereof.

6. The compounds of claim 1 wherein R represents phenyl substituted by $C(CH_3)_2C(CH_3)_3$, or an addition salt with an organic or a mineral acid thereof.

7. A therapeutic composition for the treatment of patients suffering from senile dementia, Alzheimer's disease or memory defects, comprising a cholinergically effective amount of a compound as defined in claim 1 and a pharmaceutically acceptable carrier.

* * * * *